(12) United States Patent
Clancy et al.

(10) Patent No.: US 7,896,807 B2
(45) Date of Patent: Mar. 1, 2011

(54) MULTI-CHANNEL ELECTROPHYSIOLOGIC SIGNAL DATA ACQUISITION SYSTEM ON AN INTEGRATED CIRCUIT

(75) Inventors: Edward A. Clancy, Framingham, MA (US); John A. McNeill, Stow, MA (US); William R. Michalson, Charlton, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 1414 days.

(21) Appl. No.: 11/262,493

(22) Filed: Oct. 28, 2005

(65) Prior Publication Data
US 2006/0173364 A1 Aug. 3, 2006

Related U.S. Application Data

(60) Provisional application No. 60/623,412, filed on Oct. 29, 2004.

(51) Int. Cl.
*A61B 5/00* (2006.01)
(52) U.S. Cl. .......................................... 600/300; 600/301
(58) Field of Classification Search .................. 600/300, 600/301, 323, 485; 128/920
See application file for complete search history.

(56) References Cited

U.S. PATENT DOCUMENTS

| | | | |
|---|---|---|---|
| 5,134,401 A | 7/1992 | McCartney et al. | |
| 5,409,011 A | 4/1995 | Alexeev et al. | |
| 6,029,087 A * | 2/2000 | Wohlgemuth | 607/9 |
| 6,442,195 B1 | 8/2002 | Liu et al. | |
| 2004/0133118 A1* | 7/2004 | Llinas | 600/544 |
| 2005/0096720 A1* | 5/2005 | Sharma et al. | 607/122 |

FOREIGN PATENT DOCUMENTS

| | | |
|---|---|---|
| EP | 0 738 496 A1 | 10/1996 |
| EP | 0 871 036 A2 | 10/1998 |

OTHER PUBLICATIONS

"3 V/5 V, CMOS, 500 µA Signal Conditioning ADC," Analog Devices, Inc., AD 7714, 1998.

(Continued)

*Primary Examiner* — Max Hindenburg
*Assistant Examiner* — Jonathan M Foreman
(74) *Attorney, Agent, or Firm* — Hamilton, Brook, Smith & Reynolds, P.C.

(57) ABSTRACT

A physiologic data acquisition system includes an analog input, a sigma-delta front end signal conditioning circuit adapted to subtract out DC and low frequency interfering signals from and amplify the analog input before analog to digital conversion. The system can be programmed to acquire a selected physiologic signal, e.g., a physiologic signal characteristic of or originating from a particular biological tissue. The physiologic data acquisition system may include a network interface modulating a plurality of subcarriers with respective portions of an acquired physiologic signal. A receiver coupled to the network interface can receive physiologic data from, and send control signals and provide power to the physiologic data acquisition system over a single pair of wires. The network interface can modulate an RF carrier with the plurality of modulated subcarriers and transmit the resulting signal to the receiver across a wireless network. An integrated circuit may include the physiologic data acquisition system. Also included are methods for acquiring physiologic data comprising the step of selectively controlling an acquisition circuit to acquire the physiologic signal.

27 Claims, 14 Drawing Sheets

OTHER PUBLICATIONS

Charan Langton, "Intuitive Guide to Principles of Communications: Orthogonal Frequency Division Multiplex (OFDM) Tutorial," www.complextoreal.com, 2004.

McKee, James J., et al., "Sigma-Delta Analogue-to-Digital Converters for ECG Signal Acquisition," 18th Annual International Conference of the IEEE Engineering in Medicine and Biology Society, Amsterdam, 1996, vol. 1, pp. 19-200.

Duiverman, Marieke L., et al., "Reproducibility and responsiveness of a noninvasive EMG technique of the respiratory muscles in COPD patients and in healthy subjects," *Journal of Applied Physiology*, vol. 96, No. 5, May 2004, pp. 1723-1729.

Firth, Jon and Errico, Paul, "Low-Power, Low-Voltage IC Choices for ECG System Requirements," *Analog Dialogue*, vol. 29, No. 3, 1995, pp. 1-3.

* cited by examiner

MULTI-CHANNEL ELECTROPHYSIOLOGIC SIGNAL DATA ACQUISITION SYSTEM ON AN INTEGRATED CIRCUIT

RELATED APPLICATIONS

This application claims the benefit of U.S. Provisional Application No. 60/623,412, filed on Oct. 29, 2004. The entire teachings of the above application are incorporated herein by reference.

BACKGROUND OF THE INVENTION

Various clinical and scientific disciplines monitor the electrical activity of tissues in living organisms, for example, monitoring signals arising from the heart via electrocardiography (ECG), the brain via electroencephalography (EEG), skeletal muscle via electromyography (EMG), and the like.

Common to acquisition of typical major electrophysiologic data are signal conditioning stages consisting of preamplification (mono-, bi- or multi-polar), high-pass filters (to reject motion artifact), low-pass filters (to reject noise out of band and for anti-aliasing), gain selection and digital to analog conversion. For multiple channels, multiplexing must also occur.

Typically, distinct instrumentation is designed for each electrophysiologic signal, and for different applications related to each signal—for ambulatory recording (e.g., telemonitoring), low-power design is emphasized; for multiple-channel systems, cost, size and complexity are minimized, and the like. In most cases, systems comprised of numerous discrete analog and digital electronic components per electrophysiologic channel are employed. Cost (often $500-1000/channel), size, complexity, power consumption and availability have slowed the proliferation of multiple channel systems in certain areas of medical research. For example, in ambulatory systems, power consumption can be a limiting factor.

SUMMARY OF THE INVENTION

There is therefore a need for systems and methods for acquiring electrophysiologic signals that have reduced complexity, size and power consumption, and increased flexibility compared to existing systems.

A physiologic data acquisition system comprises an analog input, a sigma-delta front end signal conditioning circuit; and a digital output. The system can be programmed to acquire a selected physiologic signal, e.g., an electrophysiologic signal characteristic of or originating from a particular biological tissue.

The physiologic data acquisition system may include a network interface modulating a plurality of subcarriers with respective portions of an acquired physiologic signal. A receiver coupled to the network interface can receive physiologic data from, over a single pair of wires. The network interface can modulate an RF carrier with the plurality of modulated subcarriers and transmit the resulting signal to the receiver across a wireless network. An integrated circuit may include the physiologic data acquisition system.

A method for acquiring physiologic data comprises selectively controlling an acquisition circuit (e.g., the physiologic data acquisition system or the integrated acquisition circuit) to acquire the physiologic signal.

In other embodiments, an physiologic data acquisition system comprises means for programming a signal conditioning circuit to condition a signal from a selected physiologic source; and means for digitizing the conditioned signal.

The disclosed invention can provide, in a single integrated acquisition circuit (acquisition IC), complete, programmable signal conditioning with an embedded analog-to-digital converter (ADC) for multiple physiologic channels. With onboard ADCs, the signal output can be in digital form. Thus, it can be digitally networked on-chip, then transmitted off-chip more reliably (typically, the digital data is encoded in a serial data stream). The design also permits many such ICs to be networked, with much of the networking hardware on-chip. Hardware wiring can be greatly reduced via the sharing of control and data information within an acquisition IC. One complete acquisition IC can condition and digitize multiple signals, and communicate via logic also embedded on the acquisition IC. This acquisition IC can be easily configured to small and large systems, can be inexpensive, can be of small size, and can require much less power than prior art systems built from discrete components. Further, the programmable nature allows the same circuit to be used for multiple electrophysiologic monitoring applications, lowering the cost of each, and allows for a single system to employ multiple, differently programmed circuits to acquire physiologic signals including electrophysiologic signals originating from different tissues in the same system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1A:
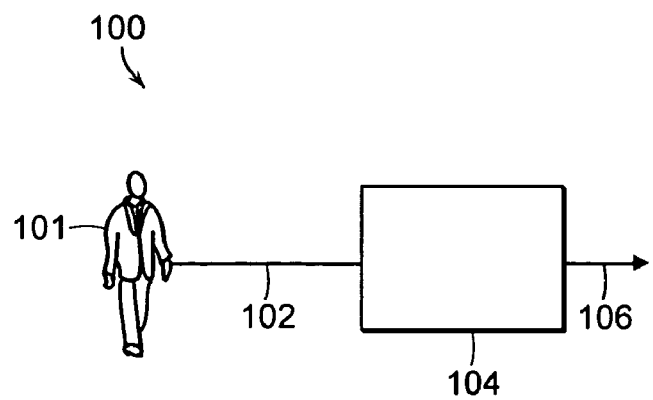
FIG. 1A depicts an embodiment of a physiologic data acquisition system 100, where analog input 102 is coupled to front end signal conditioning circuit 104 and output 106.

FIG. 1A depicts an embodiment of a physiologic data acquisition system 100, where analog input 102 is coupled to front-end signal conditioning circuit 104 and output 106. System 100 can be programmed to acquire a selected electrophysiologic signal, for example, from living tissue in a human 101. The electrophysiologic signal can be any electrophysiologic signal originating from living tissue, for example, originating in a tissue selected from heart, brain, skeletal muscle, peripheral nerve, eye, and smooth muscle of the digestive system. In some embodiments, the electrophysiologic signal originates from the heart or skeletal muscle. In other embodiments, the system can be controlled to acquire a plurality of independently selected electrophysiologic signals, e.g., originating from different tissues.

Figure 1B:
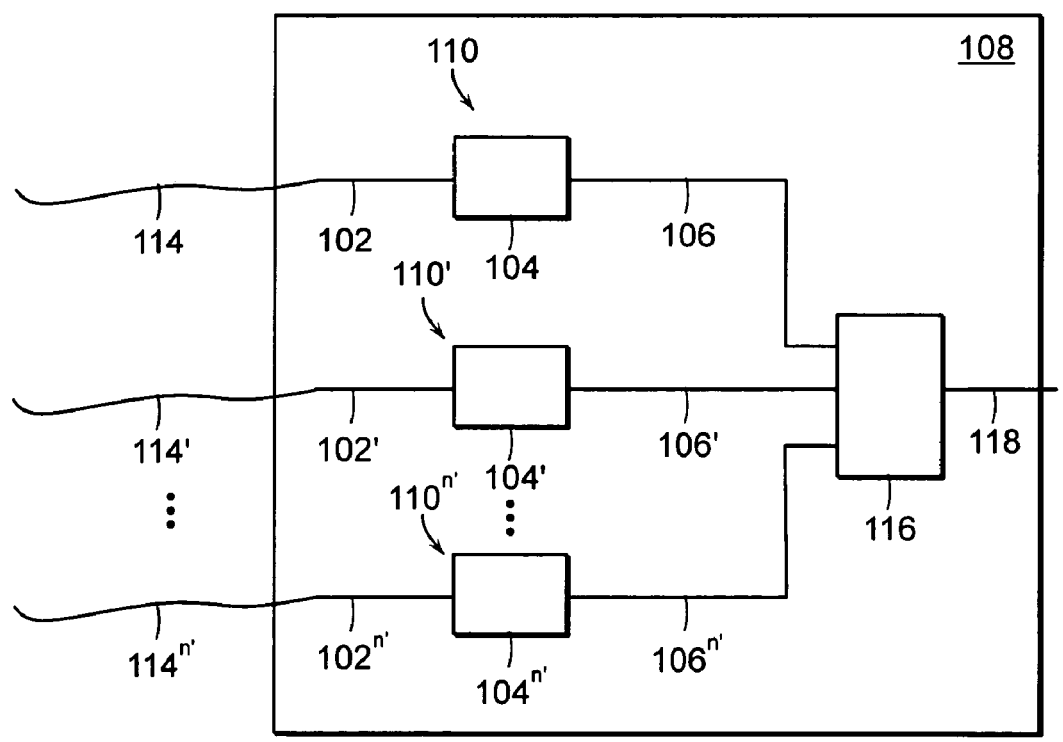
FIG. 1B depicts an integrated acquisition circuit 108 which can include acquisition channel 110, comprising input 102 (typically an analog input), front end signal conditioning circuit 104 (e.g., a conventional ADC or a sigma-delta circuit), and output 106 (digital or analog, typically digital data encoded as an analog serial data stream)

FIG. 1B depicts an integrated acquisition circuit 108 which may include acquisition channel 110, comprising input 102 (typically an analog input), front-end signal conditioning circuit 104 (e.g., a sigma-delta circuit), and output 106 (digital or analog, typically digital data encoded as a serial analog data stream). This design permits many such ICs to be networked, with much of the networking hardware on-chip.

Typically, an analog signal from input 102 may be conditioned in sigma-delta circuits, e.g., passband filtered, e.g., the signal can be filtered to remove direct current (DC) offset and low-frequency motion artifacts in the analog signal, and to reject high frequency noise out of band, provide for anti-aliasing, and the like. Also, circuit 104 can digitize the analog signal. Integrated acquisition circuit 108 can comprise a single channel 110 or can further comprise a plurality of n+1 acquisition channels, e.g., 110, 110', . . . , 110$^{n'}$ etc. For example, an integrated acquisition circuit can comprise at least 2 channels. In one embodiment, an integrated acquisition circuit can comprise at least 8 channels.

Each input 102, 102', . . . , 102$^{n'}$, can be coupled to respective electrophysiologic electrodes 114, 114', . . . , 114$^{n'}$, which can be monopolar, bipolar, or multipolar. Typically, the surface area of the subject end (the end of the electrode typically contacted to a subject to analyzed) of each electrode is at least about 1 millimeter$^2$. Such electrodes can be monopolar, bipolar, or multipolar. The surface area of the end of each electrode pole which contacts the subject can be any value consistent with the signal being acquired, the subject's skin conductivity, the electrode material etc., but is typically at least about 1 millimeter$^2$.

Each acquisition channel 110, 110', . . . , 110$^{n'}$ can be programmed to acquire a signal from an independently selected electrophysiological source. For example, acquisition channel 110 could be programmed to acquire an electroencephalography signal (from brain tissue) and acquisition channel 110' can be programmed to acquire an electrocardiography signal (from heart tissue), and the like.

Digital multiplexer 116 can be coupled to n+1 outputs 106, 106', . . . , 106$^{n'}$ of acquisition channels 110, 110', . . . , 110$^{n'}$ to combine a plurality of digital signals into a serial (typically analog but encoding digital) data stream at the serial output 118 of digital multiplexer 116. Digital multiplexer 116 can be incorporated into integrated acquisition circuit 108, as shown, or can be separate from integrated acquisition circuit 108.

Figure 1C:
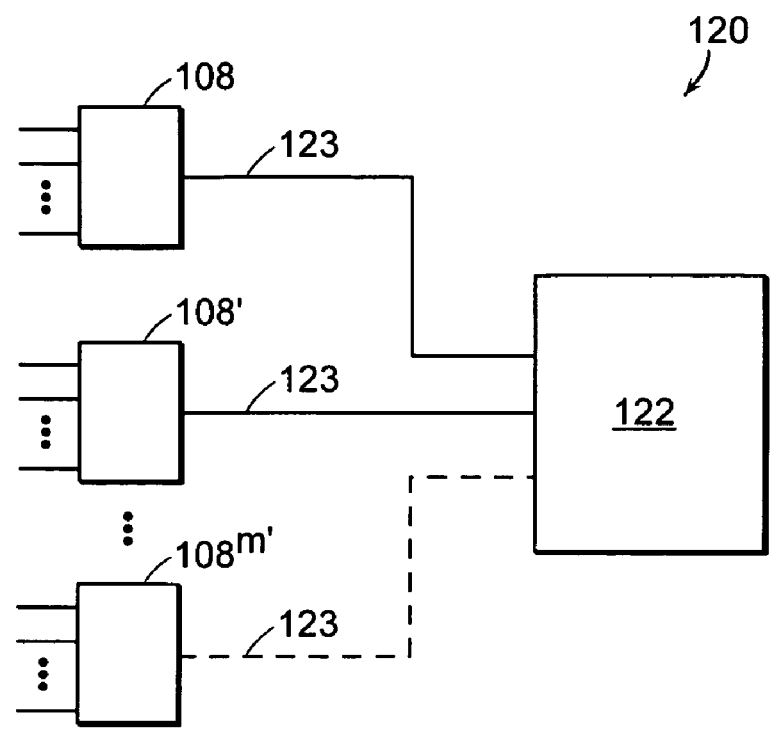
FIG 1C depicts an embodiment of a physiologic data acquisition system 120, comprising a plurality of m+1 integrated acquisition circuits 108, 108', . . . , 108$^{m'}$.

FIG. 1C depicts an embodiment of an electrophysiologic data acquisition system 120, comprising a plurality of m+1 integrated acquisition circuits 108, 108', . . . , 108$^{m'}$. Receiver 122 is networked to integrated acquisition circuits 108, 108', . . . , 108$^{m'}$, to receive plurality of serial (typically analog but encoding digital) data streams from the respective integrated acquisition circuits 108, 108', . . . , 108$^{m'}$. Receiver 122 can program each acquisition channel 110, 110', . . . , 110$^{n'}$, within each integrated acquisition circuit 108, 108', . . . , 108$^{m'}$, with a respective control signal which can be the same or different for each channel. For example, different control signals can be sent when acquisition channel 110 acquires an electroencephalography signal, when acquisition channel 110' acquires an electrocardiography signal, and the like. In some embodiments, when each channel is programmed to acquire a signal originating from the same biological tissue, each channel can still be independently programmed to account for differences between the electronics of each channel, the different locations of electrodes 114, 114', . . . , 114$^{n'}$ on a subject, and the like.

The network 123 shown between receiver 122 and m+1 integrated acquisition circuits 108, 108', . . . , 108$^{m'}$ can be wireless or wired. When the network is wired, m+1 integrated acquisition circuits 108, 108', . . . , 108$^{m'}$ can each be coupled to receiver 122, typically by a single pair of wires.

Figure 1D:
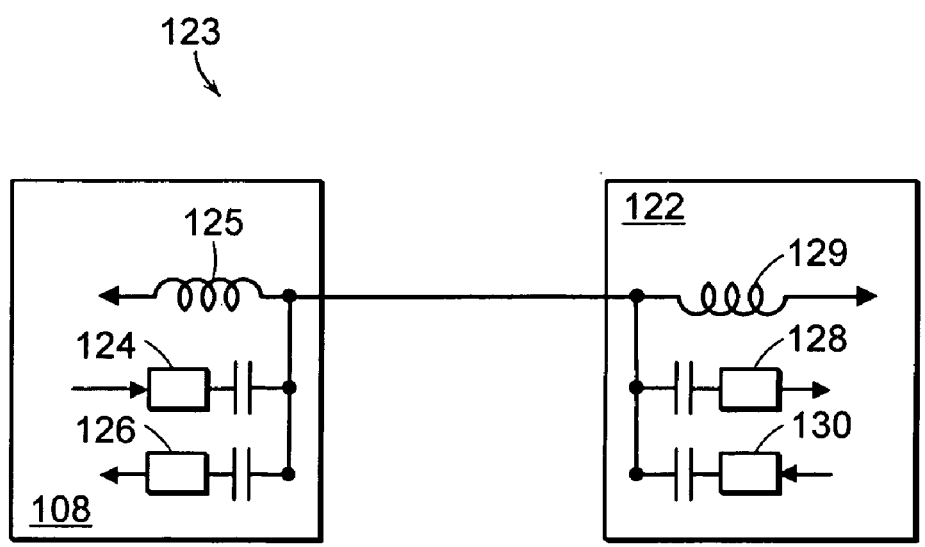
FIG 1D shows one embodiment of a network, showing detail of coupling between one integrated acquisition circuit 108 and a receiver 122.

FIG 1D shows wire pair configuration 123 in which one integrated acquisition circuit 108 is coupled to receiver 122. Each integrated acquisition circuit 108, 108', . . . , 108$^{m'}$ can comprise a data output bandpass filter 124 and a control input bandpass filter 126 corresponding respectively to a data input bandpass filter 128 and a control output bandpass filter 130 comprised by receiver 122. Receiver 122 can receive data from each integrated acquisition circuit 108, 108', . . . , 108$^{m'}$ at a data frequency corresponding to the data bandpass filters 124/128, and can control each integrated acquisition circuit at a control frequency corresponding to the control bandpass filters 126/130. Further, receiver 122 can provide power to the integrated acquisition circuits at leads 125/129 of wire pair configuration 123.

In various embodiments, physiologic data acquisition system 100 can be as described above except that one or more (in some examples all) of the various components described as comprised in an integrated circuit 108 can be part of a typical non-integrated circuit, provided that system 100 can be programmed to acquire a selected physiologic signal.

Figure 1E:
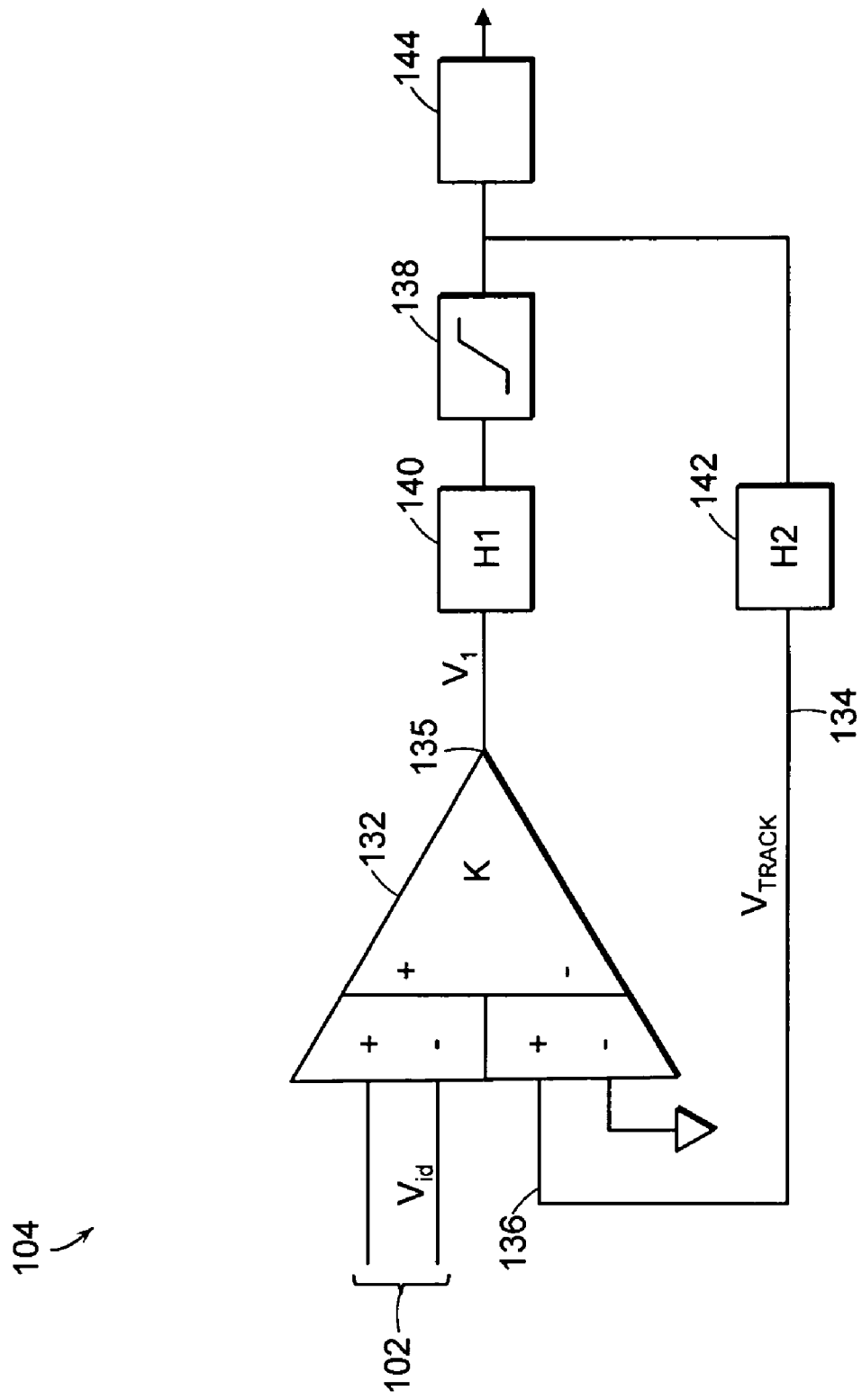
FIG. 1E shows the detail of front end signal conditioning circuit 104 comprising differential difference amplifier 132 that amplifies the difference between a differential voltage $v_{id}$ at analog input 102 and a tracking voltage $V_{TRACK}$ at subtraction loop 134.

FIG. 1E shows a sigma-delta front-end signal conditioning circuit 104 comprising (i) differential difference amplifier 132 that amplifies the difference between a differential voltage $v_{id}$ at analog input 102 and a tracking voltage $V_{TRACK}$ at subtraction loop 134 and (ii) subtraction loop 134 coupling output 135 of differential difference amplifier 132 and a subtraction input 136. The relation can be expressed as $V_1=K(v_{id}-V_{TRACK})$, wherein K is the gain.

Subtraction loop 134 can also comprise a quantizer 138, typically a one-bit quantizer. Subtraction loop 134 can also comprise at least one programmable integrator 140. Typically, programmable integrator 140 is coupled to subtraction loop 134 between differential difference amplifier output 135 and quantizer 138, and a second programmable integrator 142 can be coupled to subtraction loop 134 between differential difference amplifier input 136 and quantizer 138. Also, a reconstruction filter 144 can be coupled to differential difference amplifier output 135. Reconstruction filter 144 can be a finite impulse response filter, which can reconstruct the output of a one-bit quantizer, e.g., quantizer 138, into multibit words, e.g., 8 bit, 16 bit, and the like. Reconstruction filter 144 can also be programmed to perform other filtering functions, for example providing a programmable lowpass filter function that in combination with the subtraction loop of the sigma-delta front end (which can reject low frequency motion artifacts and direct current (DC) offset in the analog signal) can together provide a programmable bandpass filter function.

Figure 1F:
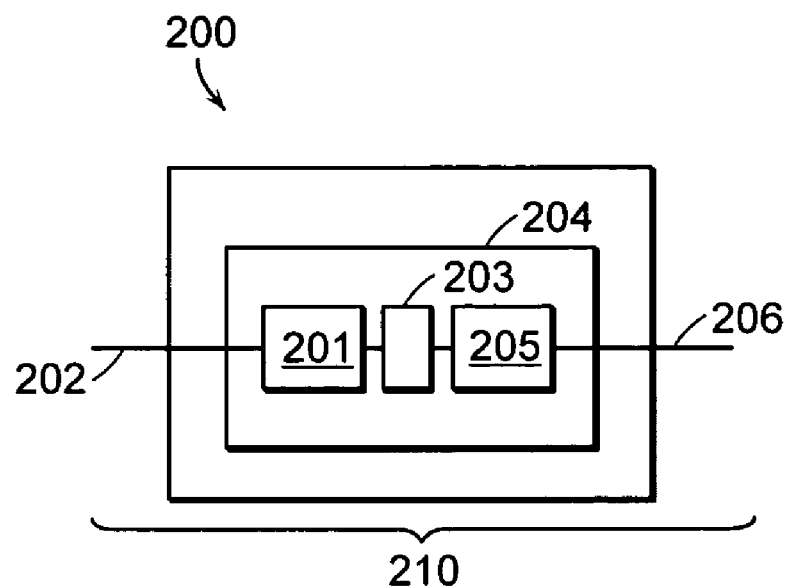
FIG. 1F depicts an embodiment of an integrated acquisition circuit for physiologic data 200, where analog input 202 is coupled to signal conditioning front end circuit 204 and digital output 206.

FIG. 1F depicts an embodiment of an integrated acquisition circuit for electrophysiologic data 200, where analog input 202 is coupled to signal conditioning front end circuit 204 and digital output 206. Integrated acquisition circuit 200 can be programmed to acquire a selected electrophysiologic signal. The electrophysiologic signal can be any electrophysiologic signal originating from living tissue, for example, originating in a tissue selected from heart, brain, skeletal muscle, peripheral nerve, eye, and smooth muscle of the digestive system. Typically, signal conditioning front end circuit 204 comprises bandpass filter 201 and an amplifier 203. In other typical embodiments, signal conditioning front end circuit 204 comprises a digitizer 205. Together, analog input 202, signal conditioning front end circuit 204 and digital output 206 comprise an acquisition channel 210.

Figure 1G:
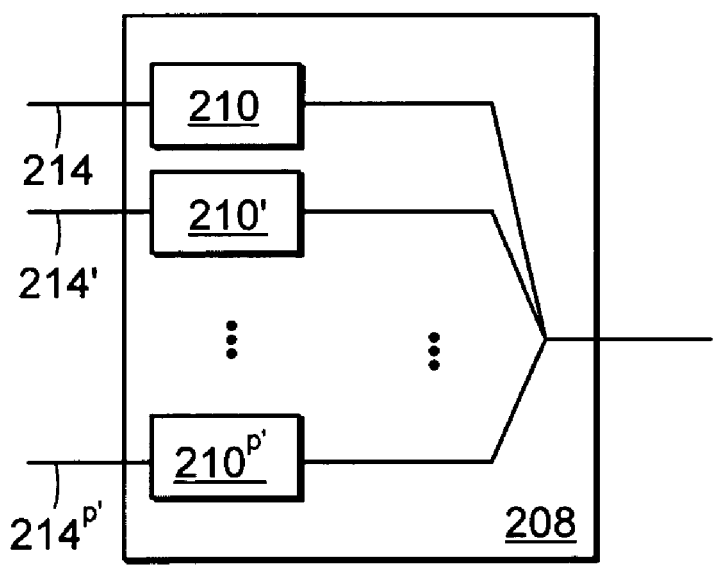
FIG 1G depicts an integrated acquisition circuit 208 which typically comprises a plurality of p+1 acquisition channels 210, 210', . . . , 210$^{p'}$, wherein typically each acquisition channel can be programmed to acquire a signal from an independently selected physiological source.

FIG. 1G depicts an integrated acquisition circuit 208 which typically comprises a plurality of p+1 acquisition channels 210, 210', . . . , $210^{p'}$ wherein typically each acquisition channel can be programmed to acquire a signal from an independently selected electrophysiological source. Each input can be coupled to respective electrophysiologic electrodes 214, 214', . . . , $214^{p'}$. In other embodiments, an integrated acquisition circuit 208 comprises the various embodiments described above for an integrated acquisition circuit 108.

The material in the following section and the figures referenced therein represent a design for various embodiments that can be constructed according to the present invention.

Electrophysiologic data have been acquired from subjects for several decades for both clinical and scientific purposes. The electrical activity can originate from many tissue sources, including the heart (electrocardiogram, or ECG), the brain (electroencephalogram, or EEG), the skeletal muscles (electromyogram, or EMG), the peripheral nerves (electroneurogram, or ENG), the eyes (electrooculogram, or EOG), and the smooth muscles of the digestive system (electrogastrogram, or EGG). Each biopotential can have a characteristic amplitude when acquired, and can occupy a characteristic frequency spectrum. Table 1 shows typical amplitudes and frequency ranges of several biopotentials. The actual amplitude and frequency ranges can vary by application—e.g., indwelling ECG/EEG/EMG electrodes tend to measure over larger frequency spans than surface electrodes. Note that all of the amplitudes of the signals are typically in the microvolts (uV) to millivolts (mV) range. In modern instrumentation systems, biopotentials are typically digitized for further processing and displayed by digital computers (or microcomputers, for the case of embedded applications).

TABLE 1

Typical amplitude and frequency ranges of several common biopotentials (Webster, J. G. (1998). Medical Instrumentation: Application and Design. New York, NY: John Wiley & Sons, Inc., p. 259).

| Biopotential | Approximate Amplitude | Frequency Range |
| --- | --- | --- |
| Diagnostic ECG | 1 mV | 0.05-100 Hz |
| Surface EEG | 100 uV | 0.1-100 Hz |
| Needle EMG | 1 mV | 100-2000 Hz |
| Surface EMG | 1 mV | 20-500 Hz |

Figure 2:
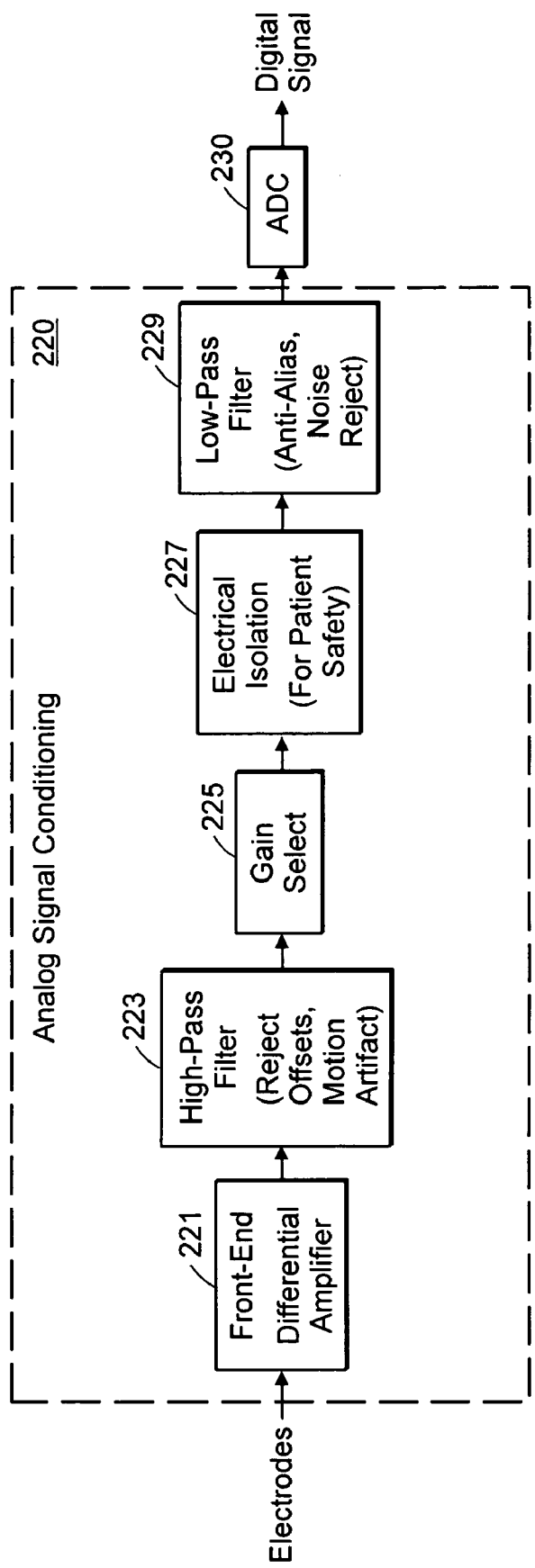
FIG. 2 (PRIOR ART) shows a typical set of biopotential instrumentation stages.

Unfortunately, the largest electrical signal present on/within the body is typically due to voltages induced from the power line (at 60 Hz frequency in North America). The power line voltage can easily be several volts (Winter, B. B. and Webster, J. G., "Reduction of Interference Due to Common Mode Voltage in Biopotential Amplifiers," *IEEE Trans. Biomed. Eng.* 30:58-62 (1983a); and Winter, B. B. and Webster, J. G., "Driven-Right-Leg Circuit Design," *IEEE Trans. Biomed. Eng.* 30:62-66 (1983b)), which can be several orders of magnitude larger than the signal of interest. For this reason, biopotentials are typically acquired using a weighted, balanced electrode configuration. One common configuration is the bipolar channel, which provides equal and opposite weights to two channels. Thus, the electrical activity from the two sites can be subtracted. Since the power line interference is typically nearly the same at each site, the subtraction ideally removes this interference. In practice, at least two factors can limit the ideal cancellation: (1) the electrode-skin impedance can be imperfectly matched at the two electrodes, and thus the actual interference voltage reaching the electronics can be different (Clancy, E. A., et al., "Sampling, Noise-Reduction and Amplitude Estimation Issues in Surface Electromyography," *J. Electromyo. Kinesiol.* 12:1-16 (2002); and Winter, B. B. and Webster, J. G., "Reduction of Interference Due to Common Mode Voltage in Biopotential Amplifiers," *IEEE Trans. Biomed. Eng.* 30:58-62 (1983a)), and (2) the electronics typically can imperfectly match the desired weights. The ability of the electronics to reject a common signal can be measured by the common mode rejection ratio (CMRR), typically expressed in dB units. When more than two electrodes are weighted and summed to form a biosignal, the sum of the weights is typically constrained to be zero, so that the common power line component can be removed from the derived signal. The electronics which perform this differential combination form the "front-end" 220 of the electronic chain, shown in FIG. 2. For smaller-amplitude biopotentials (e.g., EEG, EMG), the front-end stage 220 can typically be located as close to the signal source as possible, and connected to the remaining electronics via a cable. These front-ends can be designed as a high impedance connection to the body, so that negligible current can be drawn from the body tissues. A high-impedance difference is typically achieved via an instrumentation amplifier (e.g., AD620, Analog Devices, Norwood, Mass.). FIG. 2 shows a typical set of biopotential instrumentation stages.

Once a derived biopotential can be formed through differential combination of the electrical activity from the electrodes, the signal can be processed by analog electronics prior to digitizing. Most commonly, the next stage can be high-pass filtering (230). Electrophysiologic signals typically exhibit undesired offset potentials (a few mVs up to several hundred mVs (Metting van Rihn, A. C., "The Modelling of Biopotential Recordings and its Implications for Instrumentation Design." Ph.D. Dissertation, Technical University of Delft, The Netherlands, 1993)). If the offset is not eliminated, then signal gain (necessary to amplify the signal up to the range of the analog to digital converter (ADC) stage 230) can cause the electronics to saturate, and the signal can be lost. In addition, motion artifact can often be superimposed on the signal, and can also lead to saturation within the electronics. For appropriate signals (e.g., EMG) the high-pass filter 223 can be configured to also eliminate power up to 10-30 Hz, or even higher (e.g., needle EMG recordings often move the high-pass cut-off frequency above the power line frequency). Typically, second- to fourth-order, linear, active (utilizing operational amplifiers), high-pass filters can be selected. Some applications build the high-pass characteristic into the front-end differential amplifier 221, and some applications can require higher-order filtering (e.g., when vibration is purposely induced (Zhang, L. Q. and Rymer, W. Z., "Simultaneous and Nonlinear Identification of Mechanical and Reflex Properties of Human Elbow Joint Muscles," *IEEE Trans. Biomed. Eng.* 44(12):1192-1209 (1997)).

After high-pass filtering (223), a selectable signal gain 225 can be applied (to increase the amplitude to the range of the ADC 230, the signal can be electrically isolated (for patient safety) (227) and can be low-pass filtered (for anti-aliasing and to remove out-of-band noise)(229). The desired cut-off frequency of the low-pass filter can depend on the biopotential (see Table 1), the particular application and the sampling rate of the ADC 230. If proper anti-aliasing can be accomplished in the analog hardware, additional low-pass filtering for noise rejection could always be accomplished after the signal is digitized. The signal can then be digitized.

Figure 3:
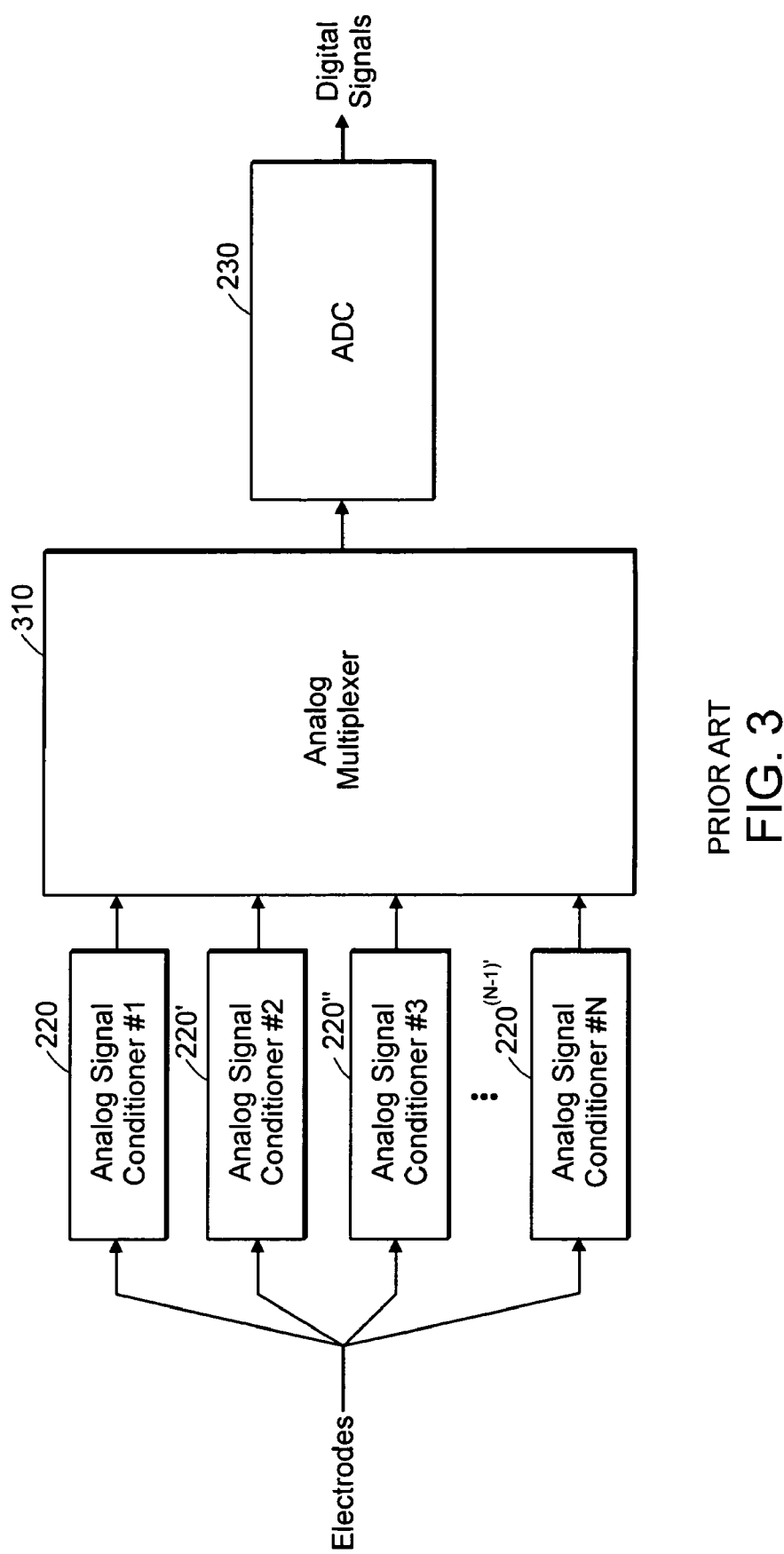
FIG. 3 (PRIOR ART) shows that when the number of channels are limited, one typically multiplexes the analog channels prior to the ADC.

It is common to acquire multiple channels of electrophysiologic activity. When the number of channels are limited, one typically multiplexes the analog channels 220, 220', 220'', . . ., 220$^{(N-1)'}$ in an Analog Multiplexer 310 prior to the ADC 230, as shown in FIG. 3. For large numbers of channels, a similar arrangement can be used, however the electrical isolation stage 227 (FIG. 2) can typically be removed from the signal conditioning block. Instead, signal isolation can be provided to the digital signals that arise from the ADC 230. Analog signal isolation is generally expensive, large in size and can consume considerable power.

Overall, power consumption for such component-based systems is typically 3-6 W for 16-channel systems (e.g., see systems by Grass-Telfactor, West Warwick, R.I.; or Delsys, Boston, Mass.). CMRR is generally above 80-90 dB. Input referred noise, evaluated by shorting the two bipolar inputs, is typically below 1-2 uV RMS over the surface EMG frequency band.

Conventional instrumentation design via discrete electronic components (i.e., the operational amplifiers, resistors, capacitors, etc. that comprise the data acquisition stages described above) is now a mature bioinstrumentation field. Existing designs have served many applications well, with numerous strengths and weaknesses known to the art. The strengths typically include robust performance from well-established designs and design practices, ease of availability of the component parts, progressive decrease in component size (e.g., surface mount packages vs. Dual In-Line Packages (DIPs) and well-established performance expectations. In this regard, existing designs can be adequate when a limited number of channels are used in non-ambulatory situations (in which size is not critical and the device can be powered from a wall outlet).

Two major limitations can be related to ambulatory applications and large electrode array systems. In ambulatory situations, size/weight and power consumption can constantly challenge the usable life of the equipment. With the aging of the U.S. population, decrease in the length of hospital stays and increased treatment occurring outside of the conventional clinical practice setting, the need to remotely monitor individuals outside of the clinical setting is increasing (e.g., Louis, A. A., et al., "A Systematic Review of Telemonitoring for the Management of Heart Failure," *Eur. J. Heart Fail.* 5:583-590 (2003)). Other examples of critical telemonitoring applications include:

1. Monitoring soldier health. The U.S. military is interested in long-term physiologic monitoring of soldiers while in the field. For example, a large percentage of deaths to medics occur when a medic is attempting to rescue an apparently injured soldier who is already dead. A global, remote indication of health, such as ECG-based heart rate, would alleviate this problem. Systems can be low power (a soldier can not be expected to change batteries frequently) and unobtrusive in size. Conventional ECG instrumentation can draw significant power and can limit the duration of time between battery replacement/recharging. Conventional systems can also be larger and heavier.

2. Monitoring emergency first responders. The risk of serious health events (e.g., cardiac ischemia) and injury to firefighters is well recognized. It can be desired to have a mechanism to monitor physiologic health remotely when firefighters enter a building. Again, low power, small size/weight apparatus for ECG monitoring can be desirable.

For systems which can include many electrophysiologic channels (tens, hundreds or potentially even thousands), compromises typically must be made. In some fields, ECG and EEG for example, large array systems are available (e.g., for cardiac mapping studies—see Dixit, S. and Callans, D. J., "Mapping for Ventricular Tachycardia," Card. *Electrophysiol. Rev.* 6:436-441 (2002)) for a recent review of ventricular tachycardia mapping studies), but can be expensive and complex to design and construct. Even in large systems, the cost per channel can often be $500-$1,000. Per channel cost can tend to decrease as the number of channels increases; but, cost and complexity can certainly tend to limit the pervasive use of large array systems. In other fields (e.g., EMG), commercial array equipment is typically only available as custom instrumentation for restricted applications.

A number of fields can benefit from replacing existing electronic instrumentation with a markedly smaller, lower power, less-expensive system. In addition, reducing the number of components and wired connections needed to implement a circuit can decrease cost and increase reliability. Conventional electrophysiologic circuits are ubiquitous, thus noticeable improvements can benefit many physiologic monitoring fields. For electrophysiologic array application, a multiple-channel mixed-signal acquisition IC for complete data acquisition as disclosed herein could be an enabling technology.

Specialized ICs for the sensing, recording and processing of neural electrode arrays have emerged in the past few years (see Wise, K. D., et al., "Wireless Implantable Microsystems: High-Density Electronic Interfaces to the Nervous System," *Proc. IEEE* 92(1):76-97 (2004) and Mohseni, P. and Najafi, K., "A Fully Integrated Neural Recording Amplifier with DC Input Stabilization," *IEEE Trans. Biomed. Eng.* 51:832-837 (2004) for recent reviews). These ICs can incorporate embedded multiple-channel sensing electrodes and analog processing. Most recently, these devices have also included analog signal multiplexing, digitizing and telemetry. To facilitate the requirements of chronic implantation (ultra low power, small size), these ICs are typically designed for their specific purpose. In particular, they typically have gain and fixed passband selections appropriate, for only neural signals. In addition, array recording of neural signals for this application typically assumes that the various recording sites are in one localized region (e.g., within a total range of a few mm maximum). The IC actually incorporates the micrometer-sized recording electrodes, and multiplexing of multiple channels is accomplished on-chip via an analog multiplexer. This architecture can be efficient for this application, as the user need not connect any signal inputs (they are provided) and only a small number of signal outputs. For many patient monitoring applications, however (cardiac mapping, surface EEG and EMG), the various recordings sites are typically more dispersed (over several or tens of cm) and the electrodes are typically distinct from the amplifying electronics. The recording electrodes can often be 2-10 mm in diameter—far too large for integration into the IC. The IC must have an explicit input for each electrode, and the electrodes are typically dispersed. Thus, it can be more efficient to disperse multiple ICs about the areas that are being monitored. Each IC might process the electrophysiologic data from a few electrodes, then communicate this information efficiently to a central receiving station. Therefore, an architecture that facilitates several multiple-channel ICs is required.

Electronics manufacturers have begun mixing analog and digital functions on the same IC for some programmable (non-electrophysiologic) data acquisition applications, e.g., AD7714 Signal Conditioning ADC (Analog Devices, Norwood, Mass.). This IC can accept analog inputs (single-ended or differential), apply a programmable gain, digitize the signal, permit some limited digital low-pass filtering, and then communicate the output signal via a serial bus. Several aspects of the ICs function can be programmed.

Figure 4:
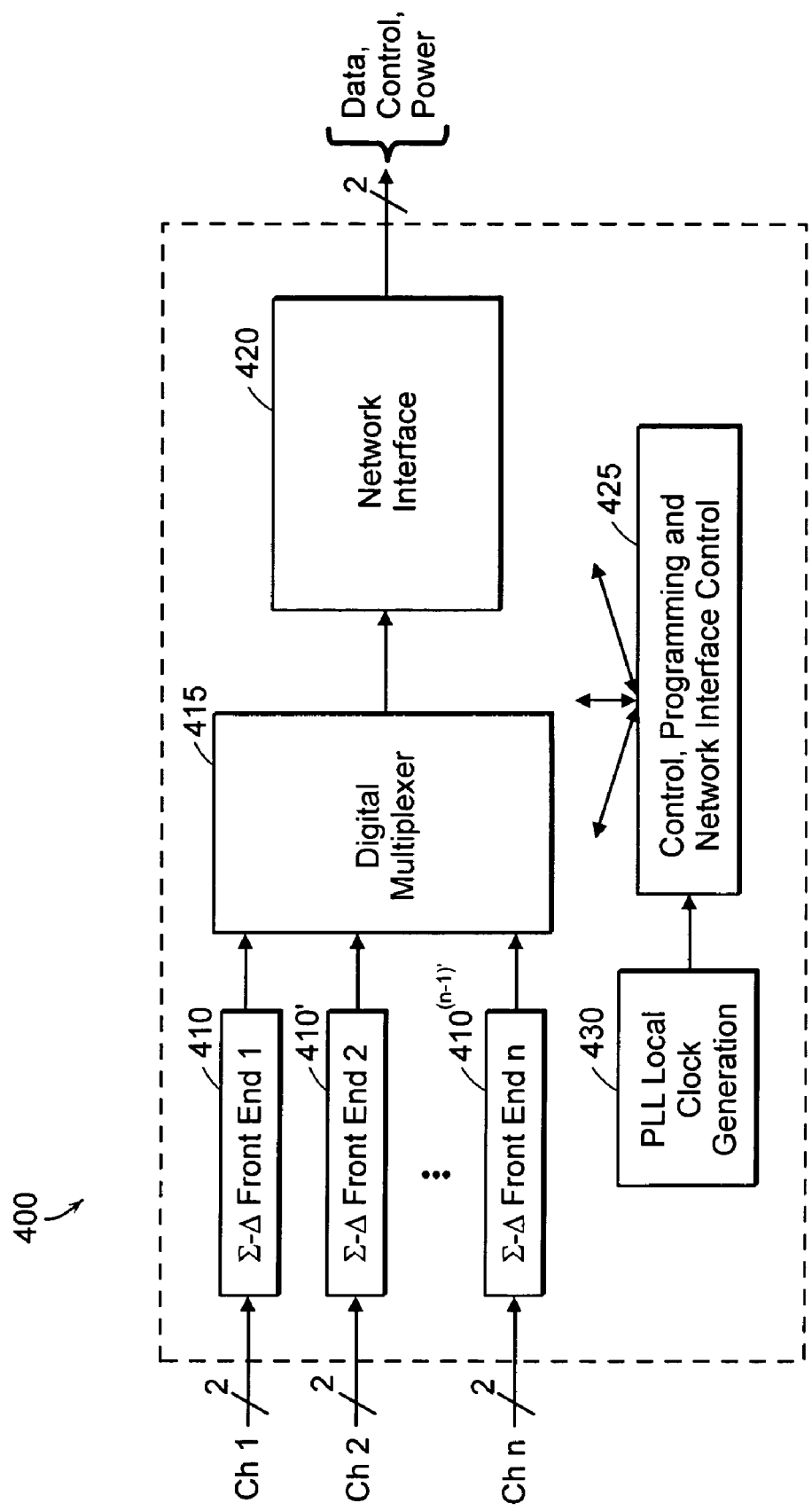
FIG. 4 shows an overall block diagram of an integrated acquisition circuit of an embodiment of the invention.

A new mixed-signal acquisition IC for electrophysiologic data acquisition is constructed and tested. The acquisition IC acquires multiple bipolar electrophysiologic channels (n is 8 or more in a prototype system), digitizes the signals, and communicates the signal samples off-chip such that these output signals are digitally networkable from a plurality of identical sensors. FIG. 4 shows an overall block diagram of the acquisition IC 400. Each input channel (Ch 1, Ch 2, ..., Ch n) can be mono-polar, bi-polar or multi-polar inputs from electrodes. In some embodiments, the mono-polar, bi-polar or multi-polar function of each electrode can be selectable, in some embodiments, programmably selectable. Each input can be processed through "Sigma-Delta Front End" circuits $410, 410', \ldots, 410^{(n-1)'}$. These circuits can accept the analog signal pair as inputs, bandpass the signal and convert the signal to the digital domain. In the digital domain, the n signals can be digitally multiplexed into one digital stream in the "Digital Multiplexer" 415. The signal is then communicated off-chip via the "Network Interface" 420. All chip functions are controlled via a control block (labeled "Control, Programming and Network Interface Control" 425 in FIG. 4) that is bidirectional. In each acquisition IC, a phase locked loop (PLL) 430 can be used to generate a local clock from the digital communication (McNeill, J., "Jitter in Ring Oscillators," *IEEE Journal of Solid-State Circuits* 32:870-879 (1997)). Data, control and power inputs/outputs can be shared by two connections to minimize wiring requirements in array systems. Although the communications functions can be implemented in this example in a wired system, the architecture can be migrated to a wireless environment. In some embodiments, most of the Sigma-Delta Front End circuits $410, 410', \ldots, 410^{(n-1)'}$, the on-board clock 430, and associated control 425 can be fabricated on a mixed-signal acquisition IC. The Digital Multiplexer 415 and the Network Interface 420 can be implemented on a Field Programmable Gate Array (FPGA) or within a Digital Signal Processor (DSP), which can facilitate rapid prototyping and flexibility for digital systems. In other embodiments, additional or all stages can be integrated on one mixed-signal acquisition IC. Additional details of the major acquisition IC sections follow.

Figure 5:
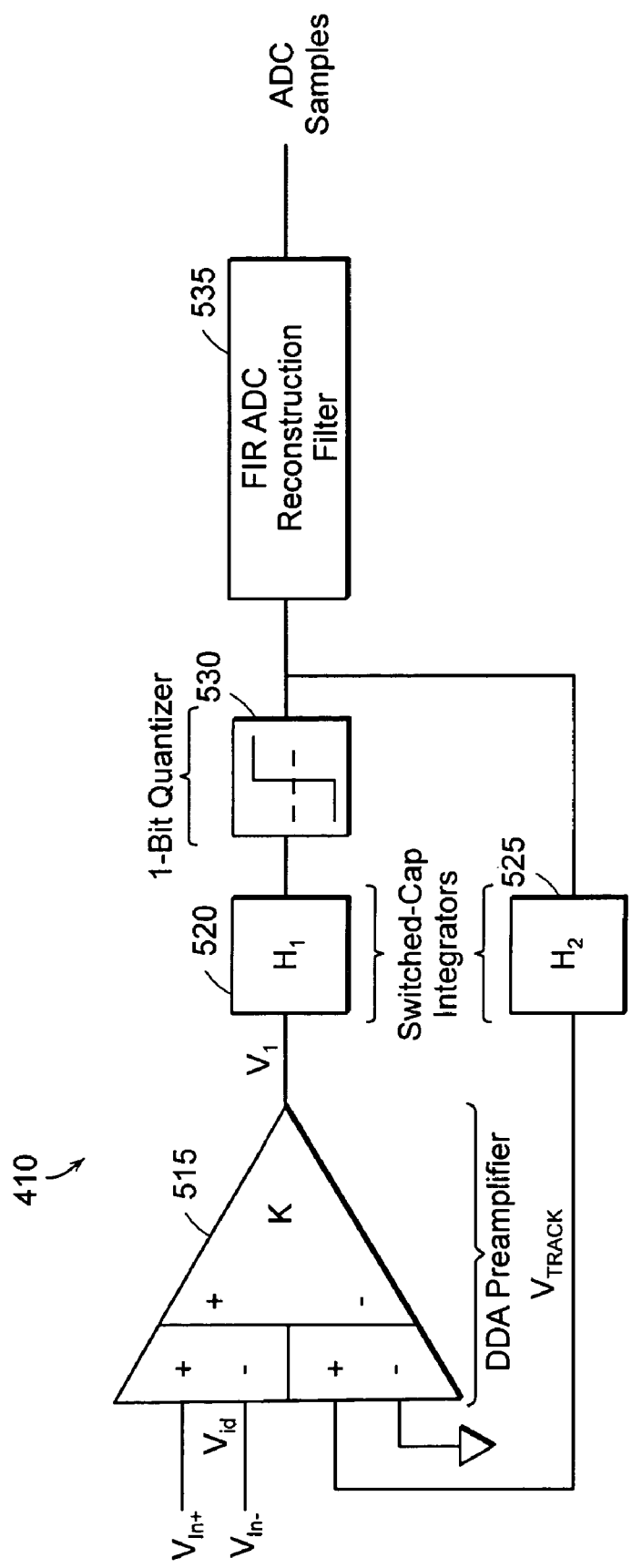
FIG. 5 shows a block diagram of a Sigma-Delta Front End signal conditioning circuit.

A block diagram of a Sigma-Delta Front End circuit 410 is shown in FIG. 5. The complete chip can incorporate n such channels, for example, each with a fully differential bipolar electrophysiological signal input and a 16-18-bit resolution ADC output. The digital output of each channel can be multiplexed into a single bit stream which can communicate with the outside world via a network interface.

A major problem in the art for the biopotentials described in Table 1 is the requirement for applying high gain to a small signal of interest while rejecting a large interfering signal (the DC offset and motion artifacts (Metting van Rihn, A. C., "The Modelling of Biopotential Recordings and its Implications for Instrumentation Design." Ph.D. Dissertation, Technical University of Delft, The Netherlands, 1993)) to prevent saturation of either the gain stage output or ADC input range. The typical approach is to AC couple the biopotential, thus rejecting the DC and low frequency components. Two major limitations of AC coupling are the difficulty of setting the corner frequency accurately, and the difficulty of making the corner frequency programmable.

The acquisition IC uses a new approach by providing a sigma-delta analog-to-digital converter for each signal processing channel, and combines a preamplifier and the DC and low frequency rejection functions into the subtraction function already present in the sigma-delta modulator. This scheme is shown in the block diagram in FIG. 5. Advantages of this approach include:

As will be described further below, this approach can allow digitally controlled placement of the low frequency pole(s). Thus the frequency domain performance can be programmable for different applications.

The pole location can be known precisely for compatibility with higher-order digital filtering done in post processing (e.g., in the reconstruction filter).

As long as saturation can be avoided in the sigma-delta modulator loop, arbitrary FIR bandpass filtering can be applied in the reconstruction filter.

Since AC coupling is not used, a very high input impedance amplifier can be used so that system characteristics can be much less dependent on electrode characteristics (c.f., Mohseni, P. and Najafi, K., "A Fully Integrated Neural Recording Amplifier With DC Input Stabilization," *IEEE Trans. Biomed. Eng.* 51:832-837 (2004)).

The sigma-delta modulator's single-bit digital output per channel can allow multiplexing in the digital domain (with, or without an on-board reconstruction filter), which can be performed with better signal integrity and lower power than analog multiplexing (c.f., Wise, K. D., et al., "Wireless Implantable Microsystems: High-Density Electronic Interfaces to the Nervous System," *Proc. IEEE* 92(1):76-97 (2004)).

In some embodiments, FIR filtering of the single-bit data stream (to reconstruct the 16 to 18 bit ADC word) can be done off-chip in either non-real-time (MATLAB) or real-time using a DSP chip or FPGA. The method can also be implemented directly in the chip. In addition, this reconstruction filter can be used to resample the data to an appropriate sampling rate (since the sigma-delta modulator typically inherently oversamples the data).

As is shown in the block diagram of FIG. 5, the preamplifier 515 can be implemented using a differential difference amplifier (DDA) (Ismail, M. and Fiez, T., *Analog VLSI: Signal and Information Processing*. (McGraw Hill) (1994)). This amplifier provides a fixed gain K as described by $$V_1 = K(v_{id} - V_{TRACK})$$

where $V_{id}$ can represent the differential input voltage (from the bipolar electrode contacts) and $V_{TRACK}$ can represent a voltage derived from the sigma-delta bit stream which tracks the DC and low frequency component of the input signal. The gain K can be fixed at a moderate value (e.g., 5) so that system noise performance can be dominated by the noise-optimized input stage of the DDA 515. The value of K can be determined by device geometry ratios and can be independent of process and temperature variations.

The novel aspects of this approach, implemented by using the preamp for multiple functions, can include:
  Increased signal amplitude to the ADC, improving noise performance (usual preamp function),
  Subtracting the tracking signal to reject DC and low frequency interfering signals (can permit easier selection of the high-pass filter cutoff frequency than AC coupling, and can be more reliable since the cutoff frequency is not formed from an RC time constant),
  Providing the subtraction function inherent to a sigma-delta ADC,
  Essentially, $V_{TRACK}$ can represent an estimate of the offset (DC and low frequency) component of the input signal, which can be derived from the digital output of the quantizer. Since $V_{TRACK}$ can be subtracted out, the input to the sigma-delta modulator can be $V_1 = K(v_{id} - V_{TRACK})$. The advantages of this configuration can be that:
  Gain can be applied after offset subtract, which can reduce the overload problem at the preamp output,
  The ADC can convert the signal after offset subtract, which can reduce the overload problem at the ADC input.

The H1 and H2 integrator transfer functions can be implemented with switched capacitor circuitry 520 and 525; whose coefficients can be set by well-controlled capacitor ratios. Capacitance can be switch-selectable (programmable) to allow digital control of the H1 and H2 transfer functions and thereby implement digital control of the entire transfer function of the sigma-delta modulator. Separate functions H1 and H2 can be used to provide flexibility in determining the ADC parameters and the filtering used in deriving the $V_{TRACK}$ estimate, which can determine the low frequency cutoff.

An additional benefit of using subtraction rather than AC coupling can be that a fully differential input can be used with an input impedance that is much higher than alternative (AC coupled) designs. The resulting input terminal characteristics (e.g., DC gain, high-pass cut off frequency) can become less dependent on the impedance characteristics of the electrode-skin interface (Mohseni, P. and Najafi, K., "A Fully Integrated Neural Recording Amplifier With DC Input Stabilization," *IEEE Trans. Biomed. Eng.* 51:832-837 (2004)). In this manner, a more stable and predictable amplifier can result.

In the system, each electrophysiologic input (monopolar, bipolar, or multipolar) can be connected to a highly flexible analog preprocessor (Sigma-Delta Front End) which can provide gain, filtering, analog to digital conversion and other features. The output of n Sigma-Delta Front Ends 410, 410', . . ., $410^{(n-1)'}$ (FIG. 4) multiplexed within one acquisition IC 410, can constitute a serial (digital) data stream containing the preprocessed sensor data from n channels. In order to create a system which can allow monitoring hundreds, or perhaps thousands, of sensors, it can be necessary to create a network which can allow potentially large numbers of acquisition ICs to communicate. In general, this communication can be bidirectional, as there can be both a need to receive data from each acquisition IC and to initialize (program) each acquisition IC with a control signal.

Figure 6:
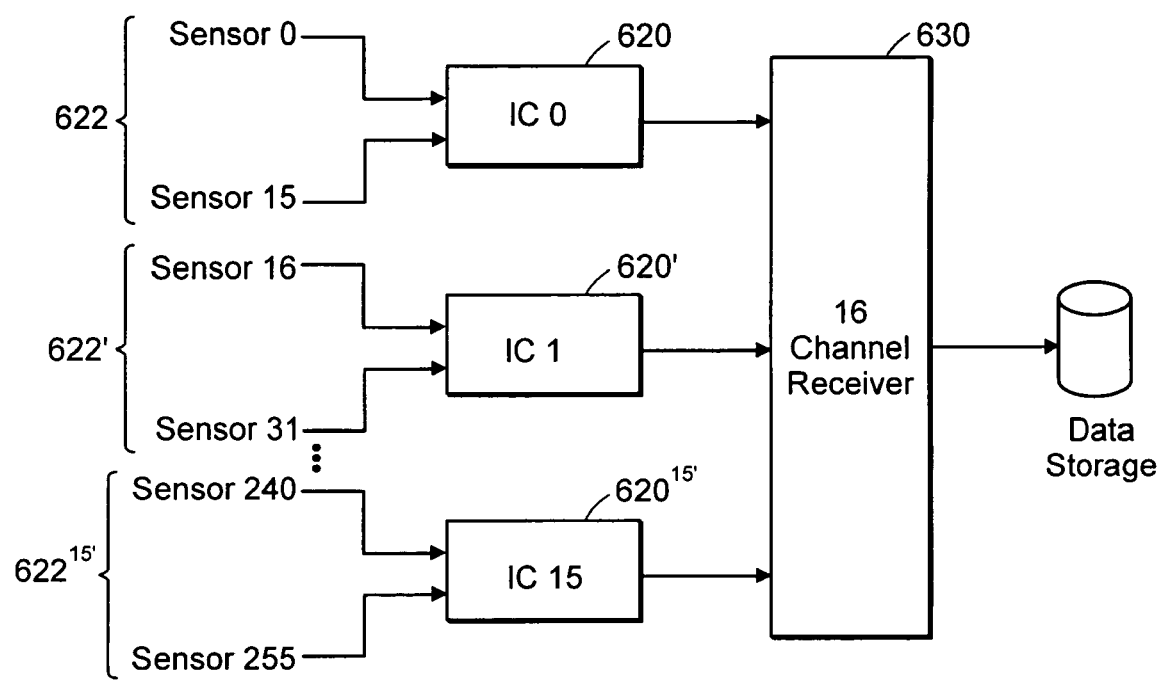
FIG. 6 shows a communications configuration (network) in which an integrated acquisition circuit of an embodiment of the invention can support up to 16 individual inputs (sensors)

One such communications hierarchy which is currently popular in modern high speed networks is the star topology (Hockney, R. W. and Jesshope, C. R., (1988). *Parallel Computers* 2: *Architecture, Programming and Algorithms*. Philadelphia, Pa.: Adam Hilger) illustrated in FIG. 6. FIG. 6 shows a communications configuration in which each acquisition IC 620, 620', . . ., $620^{15'}$ can support up to 16 individual electrophysiologic inputs (sensors). In concept, these sensors can be located a short distance from each acquisition IC 620, 620', . . ., $620^{15'}$ in order to minimize the proliferation of cables when using a large number of sensors. Thus, the acquisition ICs 620, 620', . . ., $620^{15'}$ can form respective clusters of sensors 622, 622', . . ., $622^{15'}$ which can make measurements in a certain locality. Multiple clusters can then be used to scale the system to much larger numbers of sensors without tremendously increasing the number of cables. A similar arrangement can be used in a wireless system by replacing the small number of cables between the acquisition ICs 620, 620', . . ., $620^{15'}$ and the receiver 630 with a wireless link. The number of sensors attached to each individual acquisition IC 620, 620', . . ., $620^{15'}$, and the number of channels on the receiver 630 can be based on tradeoffs between data rate, chip size, the measurement being made and the sensors being used.

Regarding the communications method, the following design goals can be considered:
  Communications latency less than about 0.1 ms.
  16-bit data transfer, in some embodiments at a maximum sample rate of about 20 kHz.
  Bidirectional data transfer (the transfer rates may be asymmetric since acquisition IC initialization can be done at a different rate from the sensor data transfer).
  Simple 2-wire interface between each acquisition IC 620, 620', . . ., $620^{15'}$ and the receiver 630.
  Easy migration to a wireless connection between each acquisition 620, 620', . . ., $620^{15'}$ and the receiver 630.
  Ability to synchronize the measurements made by all of the sensors.

In considering these goals, an approach which can avoid the need to distribute power and the need to distribute full-rate clock signals for synchronization on separate wires can be highly desirable. Current systems typically cannot avoid using separate signals because they operate using baseband digital signals. That is, digital signals can be transferred directly on the wires connecting each source to the receiver. In such a case, the usual means available to communicate can be to time multiplex data which, in turn, can imply a requirement for precise synchronization.

Figure 7:
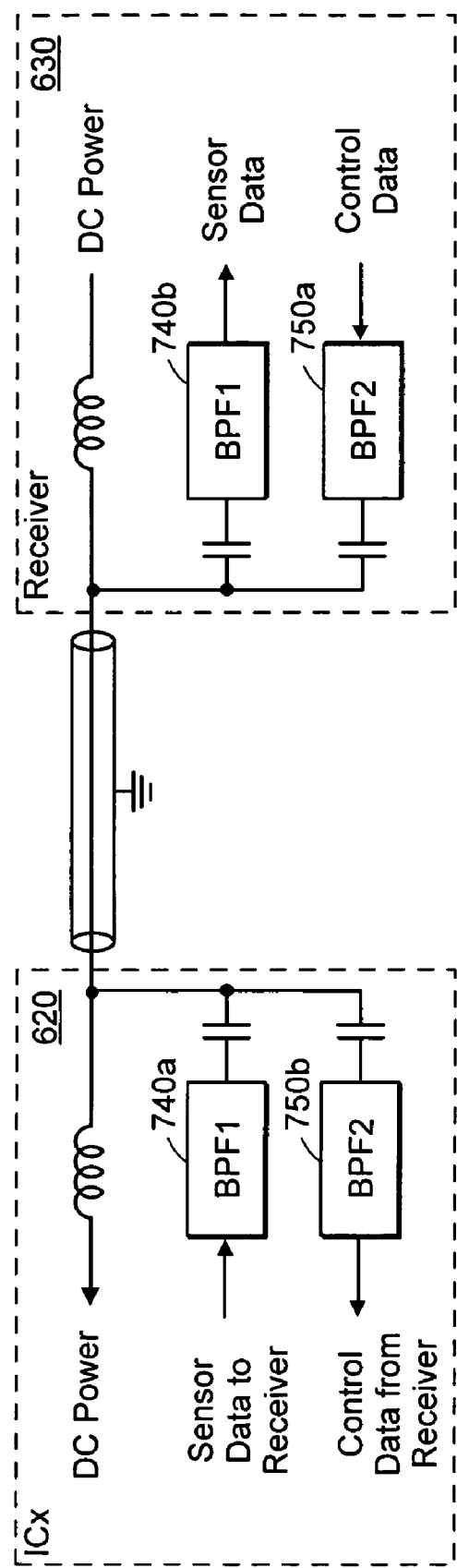
FIG. 7 shows the network where power, data and control signals can be combined onto a single pair of wires according to an embodiment of the invention.

However, the system of the invention uses the approach illustrated in FIG. 7, where power, data and control signals may be combined onto a single pair of wires. FIG. 7 illustrates a concept in which power for the acquisition ICs is supplied using only two wires. In this situation, data from the sensors can be modulated onto a carrier frequency which can lie in the center of the passband of Bandpass Filter One (BPF1) 740a. Likewise, control data from the Receiver 630 to the acquisition IC 620 can be modulated onto a carrier frequency which can lie in the center of the passband of Bandpass Filter Two (BPF2) 750*a*. The characteristics of the filters determine how closely these carriers can be placed. DC power can be provided to the acquisition ICs 620 by extracting the DC component of the composite signal (in concept, an RF choke). A significant advantage of using only two wires is that typically, only two wires need be electrically isolated (per 16 biopotential channels) to provide patient safety.

Also, FIG. 7 does not include separate full-rate clock signals being sent between the acquisition ICs 620 and the Receiver 630 for synchronization. Since using a scheme such as that in FIG. 7 can employ a modulated signal, it becomes possible to use a modulation scheme which can allow coherently detecting the signals being sent. This scheme, in turn, can allow the receiver to synchronize itself in frequency and phase to the signals being sent by each acquisition IC 620. Therefore, it can be possible to let each acquisition IC 620 generate its own local clock signal. Since the receiver 630 can be able to determine the frequency and phase adjustments needed for each acquisition IC 620 relative to the receiver's 630 own local clock, it can be possible to synchronize measurements by making corrections at the receiver 630.

Figure 8:
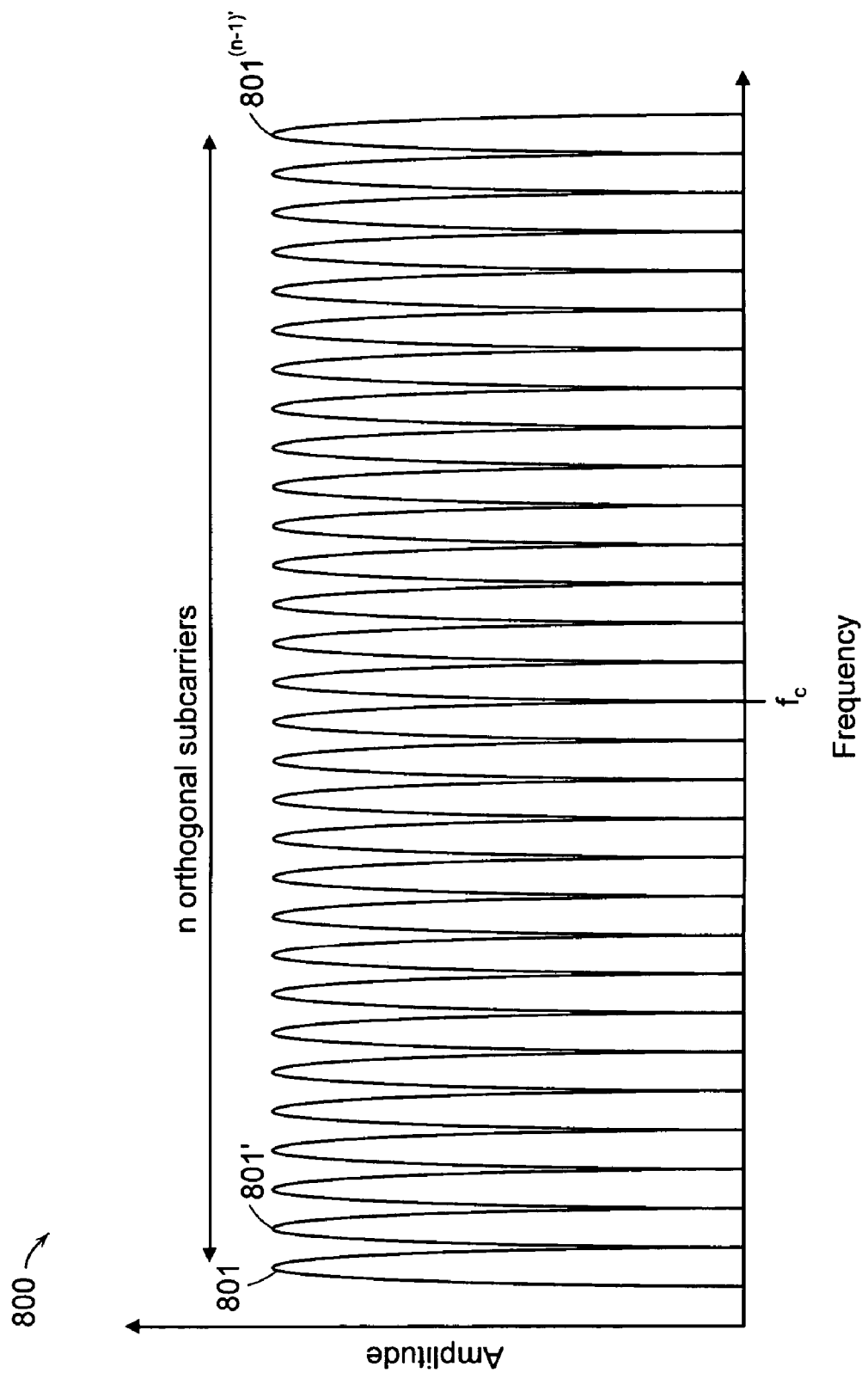
FIG. 8 depicts an Orthogonal Frequency Domain Multiplexing (OFDM) modulation scheme which can allow data to be sent over the network.

A modulation scheme which can allow data to be sent in the manner described above is Orthogonal Frequency Domain Multiplexing (OFDM). Referring to FIG. 8, in an OFDM system, many subcarriers, SCx 801, 801', ..., 801$^{(n-1)'}$ can be modulated onto a single carrier frequency, fc. Since the subcarrier frequencies can be chosen to be orthogonal (as shown in FIG. 8), there is typically no mutual interference amongst subcarriers. Thus, different channels or different ICs in one complete system can be assigned non-overlapping bands for simultaneous communication without interference.

Figure 9:
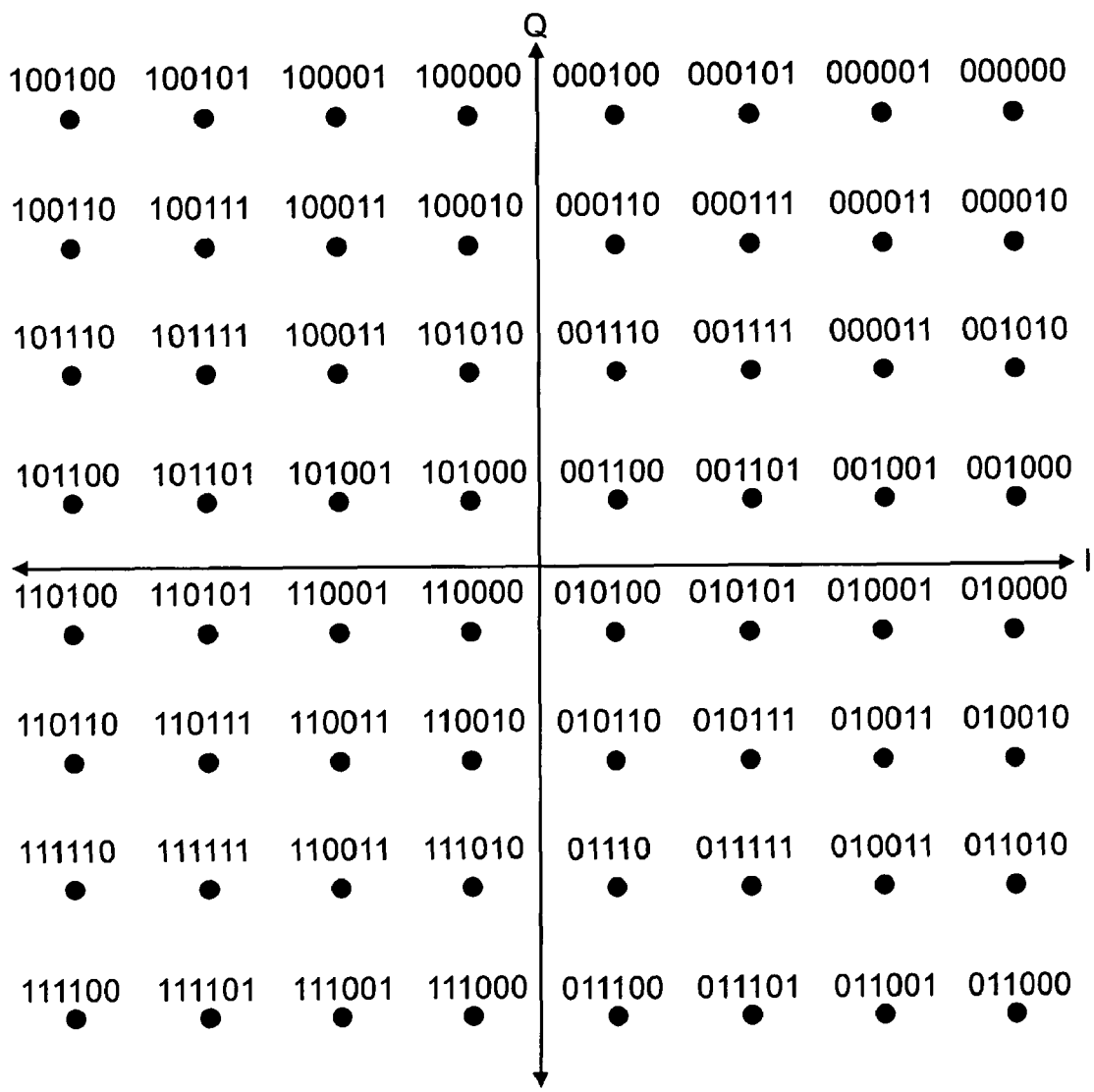
FIG. 9 depicts a representation of an ideal QAM64 constellation in which the (I, Q) location of a dot represents a unique 6-bit symbol according to a modulation technique that may be employed in conjunction with the OFDM modulation scheme of FIG. 8.

In order to communicate data, each of the orthogonal subcarriers can be modulated. In this manner, n information symbols can be transmitted simultaneously (as opposed to a single bit in a baseband digital system). To increase information carrying capacity further, a modulation technique such as QAM64 can be used to encode several bits of information into a single symbol. FIG. 9 illustrates an ideal QAM64 constellation 900 in which the (I, Q) location of a dot represents a unique 6-bit symbol.

Figure 10:
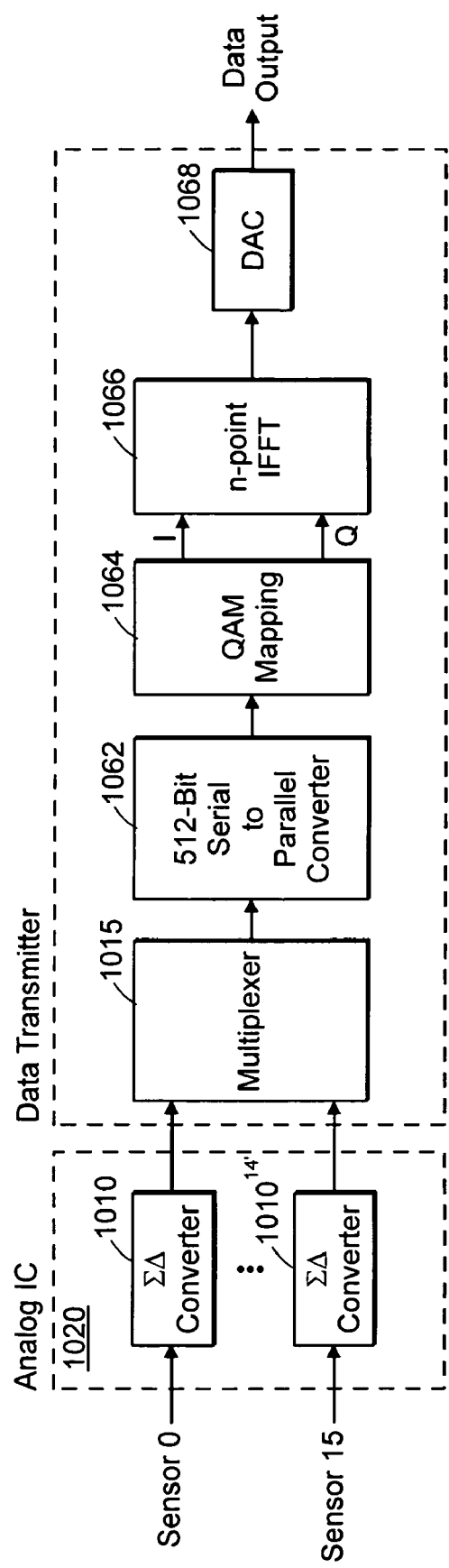
FIG. 10 depicts an embodiment of a data transmitter connecting to multiple signal conditioning circuits and employing the modulation techniques of FIG. 8 and FIG. 9.

The transmitter structure which can be employed to send data in this format is illustrated in FIG. 10. As shown in FIG. 10, serial digital data from 16 sigma-delta converters 1010, 1010', ..., 1010$^{15'}$ (the conversion to a serial bit stream is not shown) can be multiplexed by Multiplexer 1015 into a single serial (typically analog but encoding digital) data stream. For purposes of illustration, it can be assumed that each data stream is 16 bits, and that there can be 16 sensor channels being interfaced. In this case, the conversion to an OFDM signal can begin in the 512-Bit Serial to Parallel Converter 1062 by saving the most recent 512 bits from the Sigma-Delta Converters 1010, 1010', ..., 1010$^{15'}$. Next, these data can be mapped into in-phase (I) and quadrature-phase (Q) data in the QAM Mapping block 1064. Assuming a QAM16 mapping, this operation can reduce the 512 bits to 128 I,Q pairs. These I,Q pairs can be sent to a 128 point complex IFFT 1066 which can convert the now modulated subcarriers into a time domain signal. The time domain signal (typically analog but encoding digital after being processed by a DAC 1068) can then be output to the receiver as shown in FIG. 7.

Figure 11:
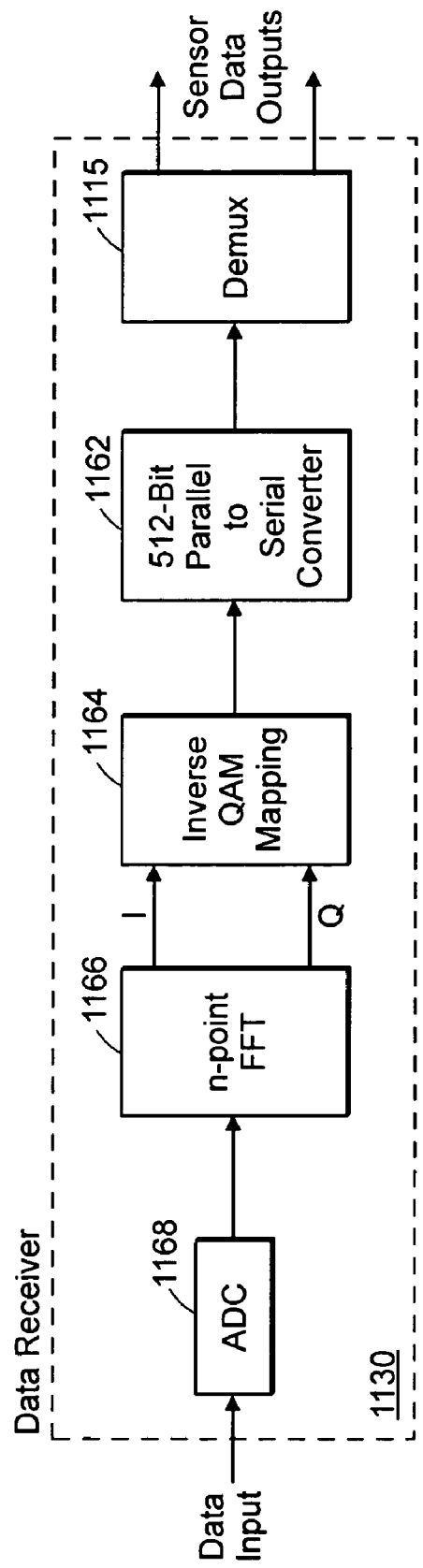
FIG. 11 depicts an embodiment of a data receiver wherein the data receiver is the inverse of the transmitter.

The receiver structure 1130 can be the inverse of the transmitter, for example as shown in FIG. 11. The receiver 1130 includes a Demultiplexer 1115, a 512-Bit Parallel to Serial Converter 1162, an inverse QAM Mapping block 1164, a 128-point complex FFT 1166, and an analog-to-digital converter (ADC) 1168. Using this OFDM technique, initial calculations indicate that all of the data from 256 sensor channels, sampled at 20 kHz with 16-bit resolution and 0.1 ms of latency can fit in a bandwidth of a few hundred kilohertz. Further, by leaving some subcarriers unmodulated, phase and frequency lock between the transmitters and receivers can be established to within a few hundred nanoseconds.

Representative expected performance goals for various embodiments of the device are shown in Table 2. Specifications can be tested as follows:

TABLE 2

Representative Target Performance Specifications

| Parameter | Diag. ECG | Surf. EEG | Needle EMG | Surf. EMG | Units | Comments |
|---|---|---|---|---|---|---|
| Lower $f_{3dB}$ | 0.05 | 0.1 | 100 | 20 | Hz | Digitally Programmable |
| Upper $f_{3dB}$ | 100 | 100 | 2000 | 500 | Hz | |
| Noise | ≦2.5 | ≦2.5 | ≦1.6 | ≦1.6 | µV rms | Including ADC |
| SNR | ≧52 | ≧32 | ≧56 | ≧56 | dB | FIG. 1 signal/rms noise |
| Input Voltage Range | ±400 | | | | mV | Offset + signal |
| THD | 1.0 | | | | % | 1 mV p—p input |
| CMRR | ≧85 | | | | dB | 60 Hz full scale input |
| Power Consumption | ≦90 | | | | mW | n = 16 channel IC |
| Supply Voltage | +5 | | | | V | Single supply; ±5% |
| ADC Resolution | 16-18 | | | | bits | |
| Communications Latency | <100 | | | | µsec | |
| Synchronization (Channel Skew) | <1 | | | | µsec | |

Lower/Upper f3 dB: An arbitrary waveform generator can be used to provide sine waves of appropriate amplitude; by sweeping the sine wave frequency, the upper and lower 3 dB frequencies can be measured. The arbitrary waveform generators can also be used to model the waveforms of typical biopotentials to verify the operation of the acquisition IC under typical signal conditions e.g., surface EMG modeled as a band-limited Gaussian random process (Hogan, N. and Mann, R., "Myoelectric Signal Processing: Optimal Estimation Applied to Electromyography—Part I: Derivation of the Optimal Myoprocessor," *IEEE Trans. Biomed. Eng.* 27:382-395 (1980)).

Input Voltage Range: The arbitrary waveform generator can allow the test sine wave signal to be superimposed on a DC offset level. Input Voltage Range can be tested by sweeping the DC offset level at the arbitrary waveform generator and verifying that signal operation meets specifications over a ±400 mV. offset range.

Total Harmonic Distortion (THD): THD can be tested by applying an input sine wave, performing an FFT on the digital output, and verifying that the total power at the sine wave harmonics is less than 1% of the fundamental power. The Spectrum Analyzer can be used to verify sufficient spectral quality of the input sine wave signal source.

Noise, Signal-to-Noise Ratio (SNR): The noise floor can be measured by shorting (applying zero input) the signal inputs and determining the rms standard deviation of the digital output as a function of frequency. SNR can be calculated from the ratio of total rms signal (from Approximate Amplitudes given in Table 1) to the measured noise level.

CMRR: Common Mode Rejection Ratio (CMRR) can be measured by applying a 400 mV peak, 60 Hz sine wave as a common mode signal (i.e. to both differential input terminals). The system gain (scale factor from input voltage to digital output code) for this common mode signal can be about 85 dB lower than the gain for differential input signals.

Power Consumption, Supply Voltage: Power requirements can be measured using DC instrumentation (programmable power supply, digital multimeter) while varying the supply voltage over a ±5% tolerance range.

Bit Error Rate Characterization: The error rate in the data transfer between the acquisition IC and the receiver can be determined by comparing known transmitted code words to the received codes.

Latency Measurement: Communication system latency will be measured as the time between generation of an ADC code on the acquisition IC and decoding of the transmitted ADC code in the receiver. With this measurement, we will verify that the communications system achieves the desired latency goal.

Synchronization: Synchronization (channel skew) can be measured by applying an identical sine wave signal to multiple input channels (sensors) on the acquisition IC and measuring the phase differences between the output signals. It can be verified whether the sensor data received can be synchronized to essentially the same point in time.

The following additional embodiments are contemplated.

1. Wireless Communication: The circuit design can be readily converted to a telemetered system via inclusion of an antenna, mixer and local oscillator into the acquisition IC design.

2. Bipolar vs. Monopolar vs. Multi-polar Inputs: Various examples herein include n bipolar input channels. With appropriate switching logic incorporated into the front end (c.f., the AD7714 Signal Conditioning ADC), it can be possible to allow selection of either n bipolar inputs or 2n monopolar inputs. For many array-based electrophysiologic applications, monopolar inputs can be used. In addition, multipolar inputs can also be considered, e.g., double difference amplifiers and Laplacian spatial filters.

3. Inclusion of Driven Right Leg Circuitry: Many electrophysiologic data acquisition systems can feed back a negated version of the common mode voltage into the reference electrode to reduce common mode signal interference (primarily from the power line) (Winter, B. B. and Webster, J. G., "Reduction of Interference Due to Common Mode Voltage in Biopotential Amplifiers," *IEEE Trans. Biomed. Eng.* 30:58-62 (1983a); and Winter, B. B. and Webster, J. G., "Driven-Right-Leg Circuit Design," *IEEE Trans. Biomed. Eng.* 30:62-66 (1983b)). Since ECG circuits can use the right leg electrode as the reference, this class of circuitry has been called a driven right leg (DRL). DRL circuits typically can be analog in design, as typical digital sampling rates are too slow to attenuate power line interference (Bertolina, M. V. et al., "Active Power-Line Interference Attenuation in Bioamplifiers," Major Qualifying Project Proposal, Dept. Elect. Comp. Eng., Worcester Polytechnic Institute, Worcester, Mass. (2001)).

4. Enhancements to the Sigma-Delta Modulator: Additional complexity in filter stages H1 and H2 can lead to higher-order bandpass filtering within the modulator stage itself. Depending on the ability of the existing design to reject offset and low-frequency (motion artifact) noise, higher-order filters can be useful. Also, there can be an inherent tradeoff between sampling rate and power consumption: as the sampling rate of the quantizer can be increased, power dissipation can be increased as well as ADC resolution. This tradeoff can be investigated, including how networked communications can function if distinct acquisition ICs within a network can be operated at distinct master rates. Also, if the feedback to the DDA can be recorded (i.e., simultaneously retained as well as the quantizer output), it can be possible to reconstruct the input signal without high-pass filtering. In other words, the sigma-delta modulator can be DC coupled. If this option can be made programmable, then the same acquisition IC can also be utilized as a stand-alone signal acquisition IC for DC coupled biomedical signals such as blood pressure and pulse oxymetry.

5. Enhancements to the Network Interface: In the above example the network interface includes signal sampling of about 20 kHz per channel. This rate can be rather conservative for most signals (e.g., surface ECG/EEG/EMG) but was chosen to be inclusive of all applicable biopotentials. With this rate, direct connection of each multiple-channel acquisition IC to the receiver can be appropriate to limit bandwidth on the connecting wire. If lower sampling rates are desired (e.g., 250-360 Hz for ECG), then it can be appropriate to interconnect several acquisition ICs via ring or shuffle networks (Hockney, R. W. and Jesshope, C. R., (1988). *Parallel Computers 2: Architecture, Programming and Algorithms*. Philadelphia, Pa.: Adam Hilger). These networks can reduce the amount of wiring, and further simplify system design—at the expense of a more complex communication protocol.

6. Inclusion of Overvoltage Protection: Incidental electrostatic discharge, defibrillation, electrocautery instrumentation, etc. can produce damaging currents/voltages at the signal inputs of the acquisition IC. Input protection circuits, typically shunting excess voltage/current to ground through diode clamping, can be incorporated into the circuit design.

7. Method of acquisition IC Programming: The acquisition IC in the example can be programmed for each application using registers—a volatile memory. For some applications, many aspects of the acquisition IC operation can be identical each time the acquisition IC is powered. To omit some or all of the redundant reprogramming, write-once memory and/or EEPROM can be used for storing the programming of some/ all of the programmable chip operation. For some applications, a chip might then only need be programmed once "in the factory," and thereafter need not be reprogrammed.

8. The front end circuit can be a conventional ADC circuit. Programmability can be implemented by selecting a discrete number of different components. For example, a bandpass circuit can be implemented, and an analog switch on the IC can be employed to select among various possible resistor values. The control input can select the desired switch settings. For example, by selecting among various resistors (e.g., eight appropriate resistor values), and repeating the selection at many locations in the circuit, the IC can be programmed to be selective for a variety of electrophysiologic signals.

The entire teachings of each document cited herein is incorporated herein by reference.

While this invention has been particularly shown and described with references to preferred embodiments thereof, it will be understood by those skilled in the art that various changes in form and details may be made therein without departing from the scope of the invention encompassed by the appended claims.

In addition to electrophysiologic signals, numerous other physiologically-derived signals are acquired or transduced from the body, either independently or in concert with electrophysiologic signals (see "Medical Instrumentation: Application and Design," third edition, John G. Webster, ed., John Wiley & Sons, Inc., 1998, particularly Table 1.1). For example, blood pressure and non-invasive blood oxygen saturation (SaO2) measurements are commonly acquired with ECG measurements. Many chemical measurements are transduced to an electrical signal. In addition, passing low-amplitude, high-frequency current/voltage through the body and measuring the resultant current/voltage provides a measure of tissue impedance which can be used directly or, for example, to detect improperly functioning electrodes or as a means to monitor respiration (Robert Patterson, "Bioelectric Impedance Measurement," pp. 1223-1230, in "The Biomedical Engineering Handbook," Joseph D. Bronzino, ed., CRC Press, Inc., 1995; "Medical Instrumentation: Application and Design," third edition, John G. Webster, ed., John Wiley & Sons, Inc., 1998.) Each of these devices/applications produces an electrical signal that must be conditioned and processed in a manner synonymous to electrophysiologic potentials, albeit typically with DC coupling. The amplitude and frequency range of these signals is within the range that can be successfully acquired by this invention. In certain embodiments, circuitry for signal conditioning and sampling of these signals can be incorporated into the system.

What is claimed is:

1. A physiologic data acquisition system, comprising:
   a plurality of integrated acquisition circuits, a first integrated acquisition circuit in the plurality of integrated acquisition circuits including a plurality of acquisition channels, each acquisition channel being programmable to acquire a signal from an independently selected physiological source, a first acquisition channel in the plurality of acquisition channels including:
      an analog input;
      a sigma-delta front end signal conditioning circuit; and
      an output;
   a digital multiplexer coupled to each acquisition channel in the plurality of acquisition channels, the digital multiplexer combining a plurality of digital signals into a serial data stream;
   a network interface coupled to the digital multiplexer, the network interface modulating a plurality of subcarriers with respective portions of the serial data stream; and
   a receiver networked to the integrated acquisition circuits that receives a plurality of serial data streams from the respective integrated acquisition circuits, the receiver sending a plurality of control signals to each respective integrated acquisition circuit and receiving the plurality of serial data streams from each respective integrated acquisition circuit over a single pair of wires.

2. The system of claim 1, wherein the physiologic signal is an electrophysiologic signal.

3. The system of claim 2, wherein the electrophysiologic signal originates in a tissue selected from heart, brain, skeletal muscle, peripheral nerve, eye, and smooth muscle of the digestive system.

4. The system of claim 1, wherein the physiologic signal relates to blood pressure or blood oxygenation.

5. The system of claim 1, wherein the physiologic signal is light reflected from a physiologic substance.

6. The system of claim 1, wherein the sigma-delta front end signal conditioning circuit comprises a bandpass filter and an amplifier.

7. The system of claim 1, wherein the first integrated acquisition circuit further comprises the digital multiplexer.

8. The system of claim 1, wherein the first integrated acquisition circuit further comprises the network interface.

9. The system of claim 1, wherein each integrated acquisition circuit comprises a data output bandpass filter and a control input bandpass filter corresponding respectively to a data input bandpass filter and a control output bandpass filter comprised by the receiver, the receiver receiving the plurality of serial data streams from each respective integrated acquisition circuit at a data frequency corresponding to the data bandpass filters, and the receiver controlling each respective integrated acquisition circuit at a control frequency corresponding to the control bandpass filters.

10. The system of claim 1, wherein the receiver further provides power to each integrated acquisition circuit over the single pair of wires.

11. The system of claim 1, wherein each acquisition channel includes a respective sigma-delta front end signal conditioning circuit that passband filters each respective analog input signal.

12. The system of claim 1, wherein each acquisition channel includes a respective sigma-delta front end signal conditioning circuit that digitizes each respective analog input signal.

13. A physiologic data acquisition system, comprising:
   a plurality of integrated acquisition circuits, a first integrated acquisition circuit in the plurality of integrated acquisition circuits including a plurality of acquisition channels, each acquisition channel being programmable to acquire a signal from an independently selected physiological source, a first acquisition channel in the plurality of acquisition channels including an analog input, a sigma-delta front end signal conditioning circuit, and an output;
   a digital multiplexer coupled to each acquisition channel in the plurality of acquisition channels, the digital multiplexer combining a plurality of digital signals into a serial data stream;
   a network interface coupled to the digital multiplexer, the network interface modulating a plurality of subcarriers with respective portions of the serial data stream; and
   a receiver that receives a plurality of serial data streams from the respective integrated acquisition circuits, the receiver being networked to the integrated acquisition circuits by a wireless network.

14. The system of claim 13, wherein the network interface modulates an RF carrier with the plurality of modulated subcarriers.

15. The system of claim 13, wherein the physiologic signal is an electrophysiologic signal.

16. The system of claim 15, wherein the electrophysiologic signal originates in a tissue selected from heart, brain, skeletal muscle, peripheral nerve, eye, and smooth muscle of the digestive system.

17. The system of claim 13, wherein the physiologic signal relates to blood pressure or blood oxygenation.

18. The system of claim 13, wherein the physiologic signal is light reflected from a physiologic substance.

19. The system of claim 13, wherein the sigma-delta front end signal conditioning circuit comprises a bandpass filter and an amplifier.

20. The system of claim 13, wherein each acquisition channel includes a respective sigma-delta front end signal conditioning circuit that passband filters each respective analog input signal.

21. The system of claim 13, wherein each acquisition channel includes a respective sigma-delta front end signal conditioning circuit that digitizes each respective analog input signal.

22. A physiologic data acquisition system, comprising:
an analog input;
a sigma-delta front end signal conditioning circuit, the sigma-delta front end circuit including a differential difference amplifier that amplifies the difference between a differential voltage of the analog input and a tracking voltage of a subtraction loop, the subtraction loop coupling the differential difference amplifier output to a subtraction input of the differential difference amplifier; and
an output,
the system being programmable to acquire a selected physiologic signal.

23. The system of claim 22, wherein the subtraction loop comprises a quantizer.

24. The system of claim 23, wherein the subtraction loop further comprises at least one programmable integrator.

25. The system of claim 24, wherein a first programmable integrator is coupled between the differential difference amplifier output and the quantizer, and a second programmable integrator is coupled between the differential difference amplifier subtraction input and the quantizer.

26. The system of claim 22, further comprising a reconstruction filter coupled to the differential difference amplifier output.

27. An physiologic data acquisition system, comprising:
means for programming a signal conditioning circuit to condition a signal from a selected physiologic source, the signal being acquired with a first integrated acquisition circuit in a plurality of integrated acquisition circuits, each integrated acquisition circuit including a plurality of acquisition channels, each acquisition channel being programmable to acquire a signal from an independently selected physiological source;
means for digitizing the conditioned signal to produce a plurality of digital signals;
means for combining the plurality of digital signals into a serial data stream;
means for modulating a plurality of subcarriers with respective portions of the serial data stream; and
means for wirelessly receiving a plurality of serial data streams from the respective integrated acquisition circuits.

* * * * *